(12) United States Patent
Sundquist et al.

(10) Patent No.: US 10,039,887 B2
(45) Date of Patent: Aug. 7, 2018

(54) INJECTION SYSTEM

(71) Applicant: Hospira, Inc., Lake Forest, IL (US)

(72) Inventors: John Sundquist, Glen Ellyn, IL (US); Ben Rush, Wilmette, IL (US); Edward Paul Browka, Oneida, NY (US); David L. Foshee, Apex, NC (US); Gretchen E. Willard, Durham, NC (US); Stephen Myers, Austin, TX (US); Hector Rodriguez, Austin, TX (US); John Coleman Horton, Austin, TX (US)

(73) Assignee: Hospira, Inc., Lake Forest, IL (US)

(*) Notice: Subject to any disclaimer, the term of this patent is extended or adjusted under 35 U.S.C. 154(b) by 347 days.

(21) Appl. No.: 14/815,669

(22) Filed: Jul. 31, 2015

(65) Prior Publication Data

US 2016/0030677 A1    Feb. 4, 2016

Related U.S. Application Data

(60) Provisional application No. 62/031,667, filed on Jul. 31, 2014.

(51) Int. Cl.
*A61M 5/315* (2006.01)
*A61M 5/50* (2006.01)
(Continued)

(52) U.S. Cl.
CPC .... *A61M 5/31515* (2013.01); *A61M 5/31501* (2013.01); *A61M 5/31513* (2013.01);
(Continued)

(58) Field of Classification Search
CPC ............ A61M 5/5086; A61M 5/31501; A61M 5/31515; A61M 5/31513; A61M 5/508; A61M 5/31505; A61M 5/347; A61M 5/502; A61M 5/50; A61M 2005/206; A61M 2005/2073; A61M 2005/2407; A61M 2005/5073; A61M 2005/312; A61M 2005/3238
See application file for complete search history.

(56) References Cited

U.S. PATENT DOCUMENTS

| 1,921,034 A | 8/1933 | Marche |
| 3,890,971 A | 6/1975 | Leeson et al. |

(Continued)

FOREIGN PATENT DOCUMENTS

| EP | 0253949 | 1/1988 |
| EP | 0 645 152 A2 | 3/1995 |

(Continued)

*Primary Examiner* — Kami A Bosworth
*Assistant Examiner* — Alexandra Lalonde
(74) *Attorney, Agent, or Firm* — Michael R. Crabb

(57) ABSTRACT

Methods and systems for an injection system are provided. An example injection system includes a container for a pharmaceutical that is sealed at a proximal end with a plunger having a pushing surface for engaging an inner surface of the hollow body. A plunger rod extends axially from the proximal end of the container and is covered with a plunger rod cover. Removal of the cover activates the system and allows for delivery of the pharmaceutical product from the container by advancing the plunger within the container towards the seal.

13 Claims, 11 Drawing Sheets

(51) Int. Cl.
  *A61M 5/32* (2006.01)
  *A61M 5/34* (2006.01)
  *A61M 5/20* (2006.01)
  *A61M 5/31* (2006.01)
  *A61M 5/24* (2006.01)

(52) U.S. Cl.
  CPC ....... *A61M 5/5086* (2013.01); *A61M 5/31505* (2013.01); *A61M 5/347* (2013.01); *A61M 5/50* (2013.01); *A61M 5/502* (2013.01); *A61M 5/508* (2013.01); *A61M 2005/206* (2013.01); *A61M 2005/2073* (2013.01); *A61M 2005/2407* (2013.01); *A61M 2005/312* (2013.01); *A61M 2005/3238* (2013.01); *A61M 2005/5073* (2013.01)

(56) References Cited

U.S. PATENT DOCUMENTS

| | | |
|---|---|---|
| 3,937,219 A | 2/1976 | Karakashian |
| 4,044,757 A | 8/1977 | McWhorter et al. |
| 4,585,445 A | 4/1986 | Hadtke |
| 4,723,937 A * | 2/1988 | Sarnoff ............... A61M 5/2066 604/136 |
| 4,929,232 A | 5/1990 | Sweeney et al. |
| 4,931,043 A | 6/1990 | Ray et al. |
| 5,114,404 A * | 5/1992 | Paxton ................. A61M 5/315 604/110 |
| 5,250,037 A * | 10/1993 | Bitdinger ............ A61M 5/3202 604/192 |
| 5,350,367 A | 9/1994 | Stiehl et al. |
| 5,358,491 A | 10/1994 | Johnson et al. |
| 5,389,086 A | 2/1995 | Attermeier et al. |
| 5,496,286 A | 3/1996 | Stiehl et al. |
| 5,501,676 A | 3/1996 | Niedospial et al. |
| 5,531,711 A | 7/1996 | Attermeier et al. |
| 5,599,314 A | 2/1997 | Neill |
| 5,653,698 A | 8/1997 | Niedospial et al. |
| 5,688,250 A * | 11/1997 | Naganuma ............ A61M 5/24 604/200 |
| 5,730,729 A | 3/1998 | Bergstresser et al. |
| 5,785,692 A | 7/1998 | Attermeier et al. |
| 6,056,726 A | 5/2000 | Isaccson |
| 6,203,530 B1 | 3/2001 | Stewart |
| 6,305,541 B1 | 10/2001 | Tanner et al. |
| 6,585,695 B1 | 7/2003 | Adair et al. |
| 6,585,702 B1 | 7/2003 | Brunel |
| 6,613,022 B1 | 9/2003 | Doyle |
| 6,893,420 B2 * | 5/2005 | Arnisolle ............ A61M 5/2066 604/135 |
| 7,351,224 B1 | 4/2008 | Shaw |
| 7,563,253 B2 | 7/2009 | Tanner et al. |
| 7,628,772 B2 | 12/2009 | McConnell et al. |
| 7,628,782 B2 | 12/2009 | Adair et al. |
| 7,658,734 B2 | 2/2010 | Adair et al. |
| 7,988,683 B2 | 8/2011 | Adair et al. |
| 7,998,131 B2 | 8/2011 | Adair et al. |
| 8,152,486 B2 | 4/2012 | Fathallah et al. |
| 8,257,345 B2 | 9/2012 | Adair et al. |
| 8,273,061 B2 | 9/2012 | McConnell et al. |
| 8,303,572 B2 | 11/2012 | Adair et al. |
| 8,500,716 B2 | 8/2013 | Adair et al. |
| 8,882,719 B2 | 11/2014 | Manke et al. |
| 2004/0199139 A1 | 10/2004 | Fowles et al. |
| 2006/0276754 A1 | 12/2006 | Kronestedt et al. |
| 2008/0171981 A1 * | 7/2008 | Khan ................... A61M 5/346 604/111 |
| 2008/0281274 A1 | 11/2008 | Rolla |
| 2010/0065049 A1 | 3/2010 | Farieta et al. |
| 2011/0224640 A1 | 9/2011 | Kuhn et al. |
| 2012/0165753 A1 | 1/2012 | Holmqvist |
| 2012/0107783 A1 * | 5/2012 | Julian ................. A61M 5/2033 434/262 |
| 2013/0053790 A1 | 2/2013 | Karlsson |
| 2013/0082057 A1 | 4/2013 | Schiff et al. |
| 2013/0085447 A1 | 4/2013 | Manke et al. |
| 2013/0085453 A1 | 4/2013 | Manke et al. |
| 2013/0085457 A1 | 4/2013 | Schiff et al. |
| 2013/0261563 A1 | 10/2013 | Zachek et al. |
| 2013/0310758 A1 * | 11/2013 | Wozencroft ........ A61M 5/3257 604/197 |
| 2013/0338585 A1 * | 12/2013 | Wendland ............... A61M 5/24 604/111 |
| 2014/0183096 A1 | 7/2014 | Oshgan et al. |
| 2014/0290344 A1 | 10/2014 | Bonfiglioli |

FOREIGN PATENT DOCUMENTS

| | | | |
|---|---|---|---|
| EP | 0645152 A2 * | 3/1995 | ............ A61M 5/002 |
| WO | WO2007137083 | 11/2007 | |

* cited by examiner

INJECTION SYSTEM

CROSS-REFERENCE TO RELATED APPLICATION

This application claims priority to U.S. Provisional Application No. 62/031,667 filed on Jul. 31, 2014, the contents of which is incorporated by reference in its entirety.

FIELD

The disclosure relates generally to injection systems and methods for delivering a pharmaceutical product to a patient.

BACKGROUND

Pharmaceutical products are often delivered or transferred through the use of an injection system, e.g., a syringe system. Many syringe systems are sold empty. In order to deliver or transfer pharmaceutical products it thus is necessary to aspirate a desired volume of pharmaceutical product into the syringe prior to the desired delivery or transfer. For example, if the desired pharmaceutical product is stored in a standard drug vial, it is necessary that the syringe system be provided with a needle or other means for accessing the interior of the drug vial in order to allow the pharmaceutical to be aspirated into the syringe system. This extra step is time consuming and may need to be undertaken by a pharmacist rather than by the healthcare practitioner who is actually responsible for the delivery/transfer of the pharmaceutical product. In order to eliminate this extra step, some pharmaceutical products in the market today are provided in pre-filled syringe systems that eliminate the need to aspirate the pharmaceutical product into the syringe system prior to delivery/transfer to the patient.

Pre-filled syringe systems can take a variety of forms, including pre-filled glass syringes, e.g., pre-filled HYPAK™ glass syringes from Becton Dickinson and Company, pre-filled plastic syringes, e.g., pre-filled ANSYR™ syringes from Hospira, Inc., and pre-filled cartridge syringes, e.g., pre-filled CARPUJECT™ and iSECURE™ syringe systems from Hospira, Inc.

Pre-filled glass syringes and pre-filled plastic syringes present potential transportation, handling, and storage issues due to the possibility that the position of the plunger rod can be inadvertently shifted resulting in either inadvertent ejection of the pharmaceutical product or inadvertent aspiration of environmental fluids into the syringe system. In order to minimize the risk of such inadvertent movement of the plunger rod, pre-filled syringes are typically placed into an overwrap packaging.

Pre-filled syringe systems that utilize pharmaceutical cartridges or ampoules, e.g., the CARPUJECT™ and iSECURE™ syringe systems sold by Hospira, Inc., utilize specialized cartridge assemblies. These cartridge assemblies typically include an ampoule containing the pharmaceutical product. The ampoule is typically closed at the proximal end by a plunger. The distal end of the ampoule is sealed by a pierceable membrane or diaphragm. A hub system is movably positioned on the distal end of the ampoule. The hub system includes a piercing needle designed to penetrate through the pierceable membrane or diaphragm when the hub system is moved from its inactivated position to an activated position. Movement of the hub system from the inactivated position to the activated position requires that the hub system and the ampoule be moved toward one another. The hub system further includes a flow pathway in fluid communication with the piercing needle. The flow pathway is in communication with a delivery end of the hub system that can include a variety of known pharmaceutical delivery devices, including hypodermic needles or luer connectors. Additional aspects of these syringe systems are described in U.S. Pat. Nos. 5,653,698 and 7,563,253, both of which are incorporated herein by reference in their entirety.

The inventors have identified certain improvements to pre-filled syringe systems.

SUMMARY

In one aspect, the disclosure is directed to an injection system that includes a container configured to contain a pharmaceutical product. The container has a proximal end, a distal end, and an inner surface extending between the proximal end and the distal end. The injection system also includes a plunger positioned within the container. The plunger has a surface that slidably engages the inner surface of the container. The injection system further includes a plunger rod connected to the plunger. The plunger rod extends from the plunger such that at least a portion of the plunger rod is positioned externally to the proximal end of the container. The injection system still further includes a housing at least partially surrounding the container and a plunger rod cover removably coupled to the housing. The plunger rod cover encloses the portion of the plunger rod positioned externally to the container. The plunger rod cover is configured to be removed from the housing to allow access to the plunger rod. Removal of the plunger rod cover moves the container from an inactivated position to an activated position.

In a further aspect, the injection system includes a fluid seal at the distal end of the container, a hub secured to the distal end of the container, and a driver coupled to proximal end of the housing. The hub includes (i) a proximal portion defining a cavity that is configured to engage the distal end of the container, and (ii) a piercing member located within the cavity. The piercing member includes an internal fluid pathway. The hub is configured to engage the container in an inactivated position in which the piercing member does not penetrate the fluid seal, and an activated position in which the piercing member penetrates the fluid seal. The driver comprises a surface that engages a complementary surface on the plunger rod cover to advance the container in the distal direction within the housing in response to rotation of the plunger rod cover relative the housing. The distal advancement of the container causes the hub to move from the inactivated-hub position to the activated-hub position, thereby activating the injection system.

In another aspect, the disclosure is directed to an injection system including a container having a proximal end, a distal end, and an interior surface, the interior surface defining a cavity for containing a pharmaceutical product. The system also includes a plunger disposed in the cavity defined by the container, the plunger having a surface constructed to sealingly engage the interior surface of the container whereby a seal is maintained between the plunger and the interior surface of the container as the plunger is moved within the cavity. A plunger rod is attached to the plunger and extends proximally from the plunger such that a portion of the plunger rod is disposed externally to the container. The container is at least partially surrounded by a housing. A plunger rod cover defines an interior space, the plunger rod cover being removably attached to the housing. A driver is mounted on the housing, the driver being configured to engage the plunger rod cover when the injection system is in a first, inactivated state, the driver further being configured to move the injection system from the first, inactivated state to a second, activated state upon removal of the plunger rod cover from the housing.

Still further, the disclosure is directed to an injection system wherein the container has a pierceable fluid seal fluidly sealing the distal end thereof, the container further comprising a hub movably mounted to the distal end of the container, the hub having a piercing member constructed to pierce the pierceable fluid seal. The hub has a first position in which the piercing member is disposed externally to the cavity defined by the container and a second position in which the piercing member is disposed through the pierceable fluid seal whereby the interior of the cavity is in fluid communication with an external environment through the piercing member.

Even further, the plunger rod cover may be constructed to be removed by rotating the plunger rod cover relative to the injection system. In addition, the driver may include a stop surface configured to engage the plunger so as to inhibit the plunger from being removed from the container. The system may also include a tamper evident seal associated with the plunger rod cover, wherein removal of the plunger rod cover breaks the seal.

In yet another aspect, the disclosure is directed to a method of delivering a pharmaceutical product. The method includes providing an injection system that includes a container having a proximal end, a distal end, and an inner surface extending between the proximal end and the distal end. The inner surface of the container defines an interior volume containing a pharmaceutical product. The injection system also includes a plunger positioned within the container and having a surface that slidably engages the inner surface of the container. The injection system further includes a plunger rod connected to the plunger. The plunger rod extends from the plunger such that at least a portion of the plunger rod is positioned externally to the proximal end of the container. Additionally, the injection system includes a plunger rod cover removably coupled to the system and enclosing the portion of the plunger rod positioned externally to the container. The plunger rod cover is configured to be removed from the system to allow access to the plunger rod. The injection system still further includes a driver constructed to transduce rotation of the plunger rod cover to transition the injection system from an inactivated state in which the pharmaceutical product in the container cannot be delivered therefrom to an activated state in which the pharmaceutical product in the container can be delivered from the container. The method also includes rotating the plunger rod cover and removing the plunger rod cover from the injection system, thereby transitioning the injection system from the inactivated state to the activated state. The method further includes applying a distally directed force to the plunger rod in order to deliver the pharmaceutical product from the container.

These as well as other aspects, advantages, and alternatives will become apparent to those of ordinary skill in the art by reading the following detailed description with reference where appropriate to the accompanying drawings. Further, it should be understood that the description provided in this summary section and elsewhere in this document is intended to illustrate the claimed subject matter by way of example and not by way of limitation.

DESCRIPTION

Figure 1:
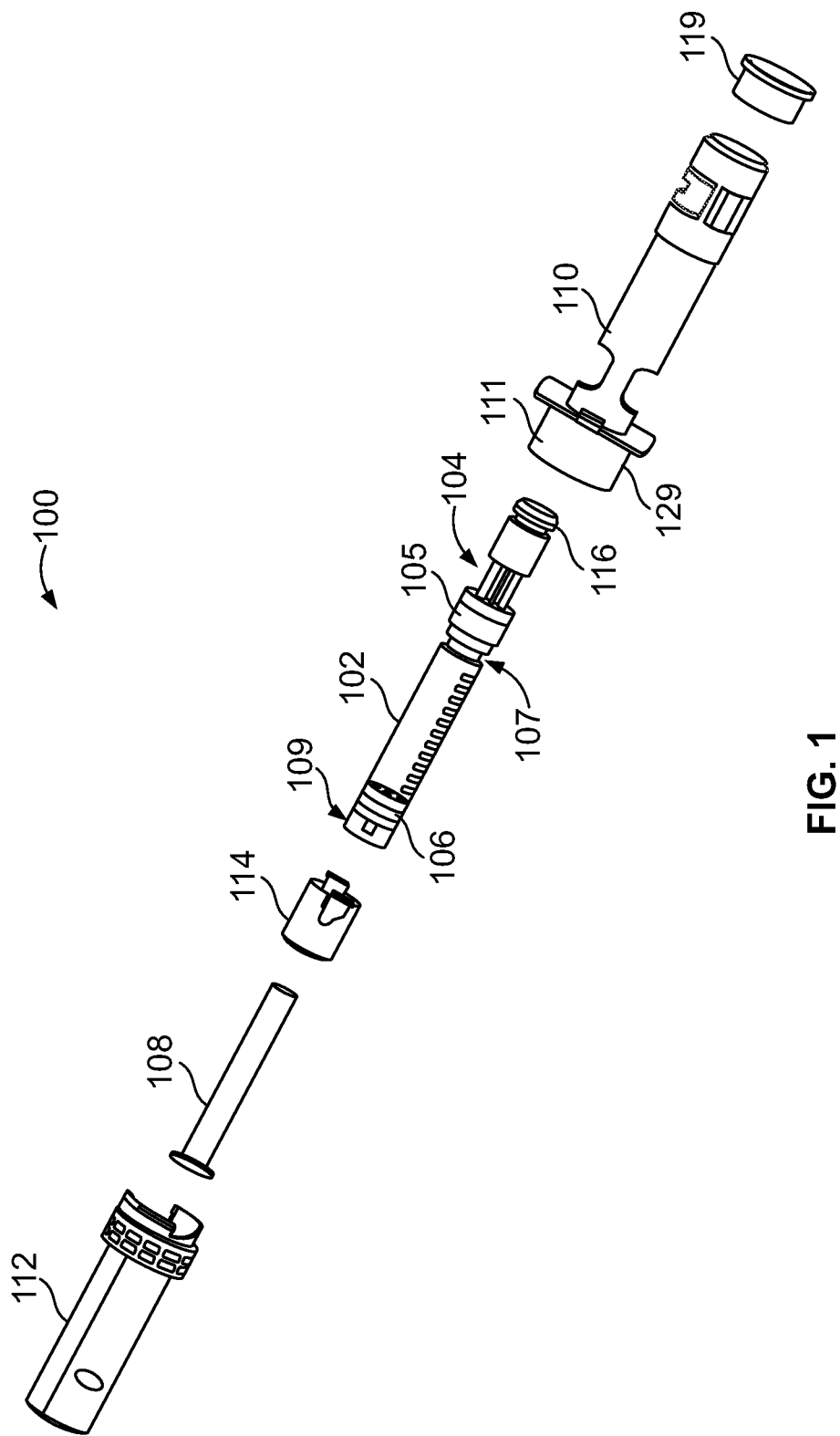
FIG. 1 is an exploded view of an example injection system.
Figure 2:
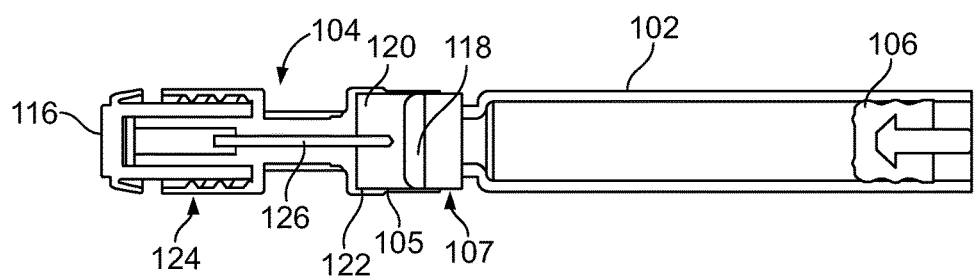
FIG. 2 is a cross section view of an example container and hub in an inactivated position.

In general, the disclosure is directed to an injection system including an assembly for delivering a dosage of a pharmaceutical product to a patient. The assembly includes a fluid container for holding a liquid pharmaceutical product, the fluid container having an elongated hollow body. The fluid container includes at least one portion having a substantially consistent cross-sectional internal dimension and shape, such as, for example, a traditional cylinder-shaped body used in a syringe, an ampoule, a drug cartridge, or other small volume medical fluid container known to those of skill in the art.

In those embodiments in which the small volume container is an ampoule or cartridge, the fluid container can be closed at a distal end thereof by a penetrable fluid seal. For example, the fluid seal may be a pierceable membrane that allows the contents to be dispensed after the fluid seal is penetrated by a suitable penetrator or needle. Alternatively, the fluid seal can be a breachable seal whereby the contents of the fluid container can be accessed by physically cutting, tearing, or otherwise compromising/opening the fluid seal. In those embodiments in which the fluid container is a syringe body, the fluid seal is optional.

At the proximal end of the fluid container, the fluid container is fluidly sealed with an axially movable plunger that engages an inner wall of the fluid container. As the plunger is moved axially toward the distal end of the fluid container, it will push liquid through an opening in the distal end of the fluid container, provided that the fluid seal (if included) on the distal end of the fluid container has been pierced, breached, or otherwise opened. As the plunger is moved axially toward the proximal end of the fluid container, it will cause fluids to be aspirated into the fluid container through the opening in the distal end of the fluid container, again provided that the fluid seal (if included) on the distal end of the container has been pierced, breached or otherwise opened. A plunger rod is attached to the plunger and extends proximally out of the fluid container. The plunger rod allows a practitioner to apply axial forces to the plunger in order to move the plunger toward the proximal end of the fluid container, thereby aspirating external fluids into the fluid container, or to move the plunger toward the distal end of the fluid container, thereby expelling fluid contents of the fluid container through the opening at the distal end of the fluid container. The medical delivery device may further include a removable plunger rod cover which is configured to prevent inadvertent movement of the plunger rod and plunger during transportation and storage.

In one embodiment, the injection system is constructed such that removal of a plunger rod cover transitions the injection system from an inactivated state to an activated state. In the inactivated state, the system is not capable of dispensing liquid in an intended manner. Activation refers to the state of the system that allows the practitioner to aspirate fluids into or dispense fluids from the fluid container. For example, in one embodiment the delivery system includes a penetrator constructed to pass through the fluid seal on the distal end of the fluid container and the delivery system is further configured such that removal of the plunger rod cap from the system causes reactive movement between the fluid seal and the penetrator so as to move the system from the inactivated state to the activated state.

As used herein, the terms "distal," "lower," and "downward" are intended to reference the end of the injection system that would be furthest from the medical professional holding injection system during use. Conversely, the terms "proximal," "upper," and "upward" are intended to reference the end of the injection system that would be nearest the medical professional during use.

The injection system may have a variety of configurations and may include several components that are pre-assembled by a manufacturer or assembler and supplied in combination to medical professionals. FIGS. 1-4 illustrate an exemplary injection system 100 having a fluid container 102 that is constructed to contain a liquid pharmaceutical product. The fluid container 102 can be constructed from a variety of known materials that are compatible with the pharmaceutical product to be contained therein. In one embodiment, the fluid container 102, or at least the interior, pharmaceutical-contacting surface 103 thereof, is constructed of glass due to the relative inactivity between glass and most pharmaceutical products. However, it will be appreciated that in certain cases it may be appropriate or necessary to use non-glass materials due to the possible interaction between the pharmaceutical product and glass. For example, the fluid container 102 can be constructed of a glass material having a non-glass material (e.g., plastic) coated or otherwise layered on its inner and/or outer surfaces, or the fluid container 102 can be constructed entirely of a non-glass, (e.g., plastic) material that is non-reactive to the pharmaceutical product to be contained in the fluid container 102. Alternatively, the fluid container 102 can be constructed of multiple plastic materials that provide for the desired lack of interaction with the pharmaceutical product to be contained by the fluid container 102. Use of such composite materials in the fluid container 102 can facilitate (i) the minimization of interaction between the fluid container 102 and the contents thereof; (ii) the optimization of breakage resistance, heat resistance, and/or other characteristics of the fluid container 102; and (iii) the optimization of the cost of the fluid container 102. Further, the fluid container 102 can have a variety of forms other than the depicted ampoule. For example, the fluid container 102 can be formed as a syringe barrel constructed to receive a pharmaceutical product therein.

Figure 3:
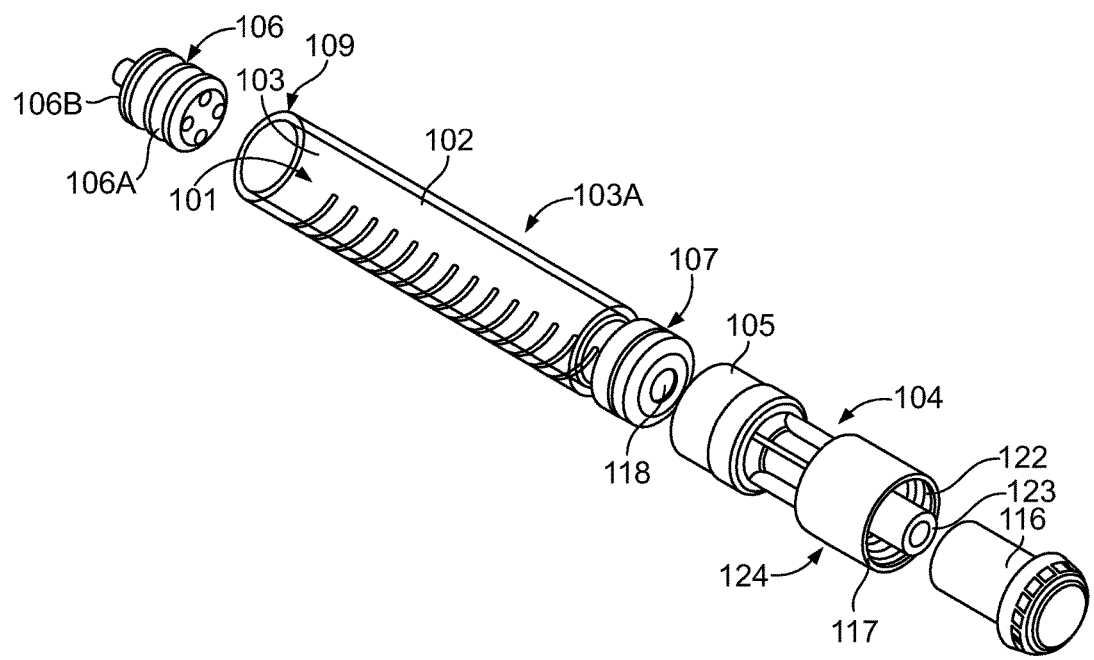
FIG. 3 is an exploded view of an example container and hub.

In the embodiment depicted in FIG. 3, the fluid container 102 is sealed at its distal end 107 with a fluid seal 118. The fluid seal 118 is constructed to be opened in at least one of a variety of manners such as piercing, rupturing, tearing, cutting, etc., as discussed in detail herein. The fluid seal 118 is constructed of a material that is compatible with the pharmaceutical product to be contained in the fluid container 102. In addition, the material must substantially prevent fluid movement from one side of fluid seal 118 to the other side of the fluid seal 118. Further, the fluid seal 118 is constructed of a material that facilitates the desired piercing, rupturing, tearing, or cutting thereof.

As depicted in FIGS. 1 and 2A, the injection system 100 includes a hub 104 constructed to be slidably mounted on the distal end 107 of the fluid container 102. The hub 104 includes (i) a proximal portion 105 defining a cavity 120 that is configured to receive and mechanically engage the distal end 107 of the fluid container 102, and (ii) a piercing member 126 positioned within the cavity 120. In this embodiment, piercing member 126 is constructed to pass through the fluid seal 118 when fluid container 102 (and fluid seal 118) is moved toward hub 104 during activation of the injection system 100. The piercing member 126 can have a variety of configurations and can be constructed of metal or plastic materials. In one configuration, the piercing member 126 is constructed of a metal material, e.g., stainless steel, and defines a fluid pathway through its interior. Another example of a piercing member 126 suitable for use with the injection system 100 is disclosed in U.S. Patent Publication No. 2014/0183096, which is incorporated herein by reference in its entirety.

In the depicted embodiments, the proximal end 109 of the container 102 may be fluidly sealed with a plunger 106. In order to provide a fluid-tight seal between the plunger 106 and the interior wall of the fluid container 102, the plunger 106 is preferably constructed of an elastomeric material that is compatible with the pharmaceutical product to be contained in fluid container 102. The plunger 106 is constructed to slide axially within the fluid container 102 while maintaining a fluid seal against the interior wall of the fluid container 102. The proximal side 106B of the plunger 106 is connected to a plunger rod 108 that extends outwardly from the proximal end 109 of the fluid container 102 such that axial movement of the plunger rod 108 relative to the fluid container 102 causes axial movement of the plunger 106 within the fluid container 102.

Figure 10A:
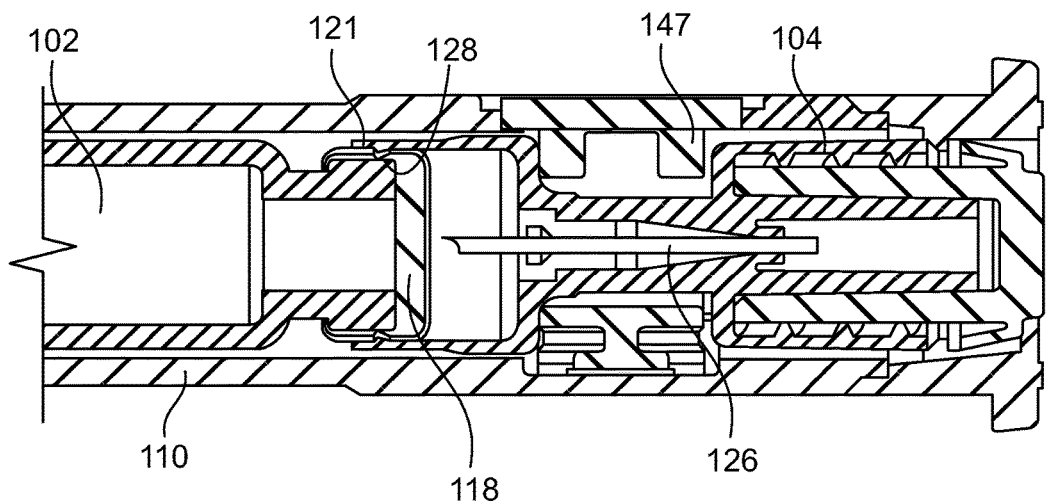
FIG. 10A is cross section view of an example hub in an inactivated position.
Figure 10B:
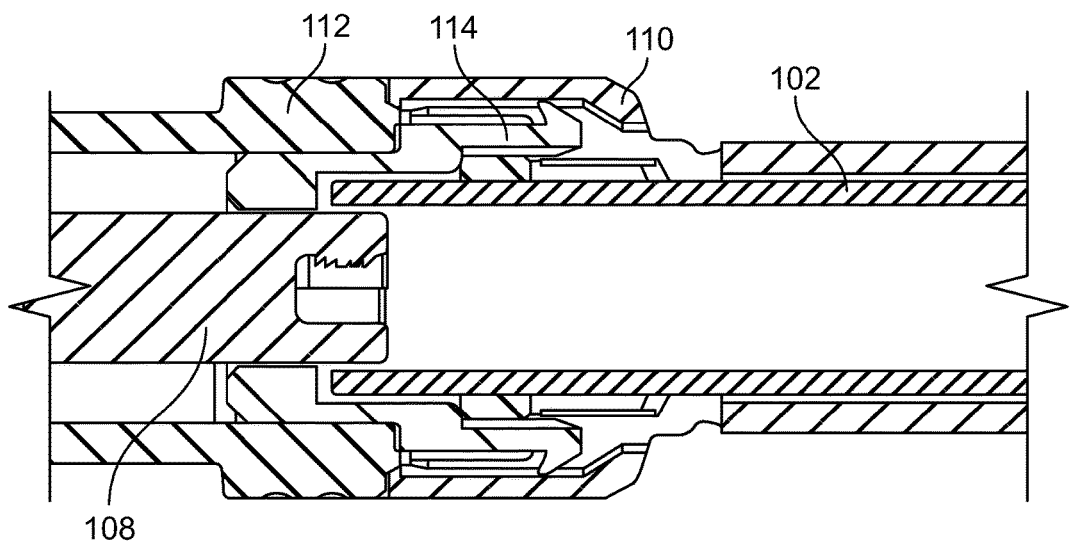
FIG. 10B is a cross section view of an example driver in an inactivated position.
Figure 10C:
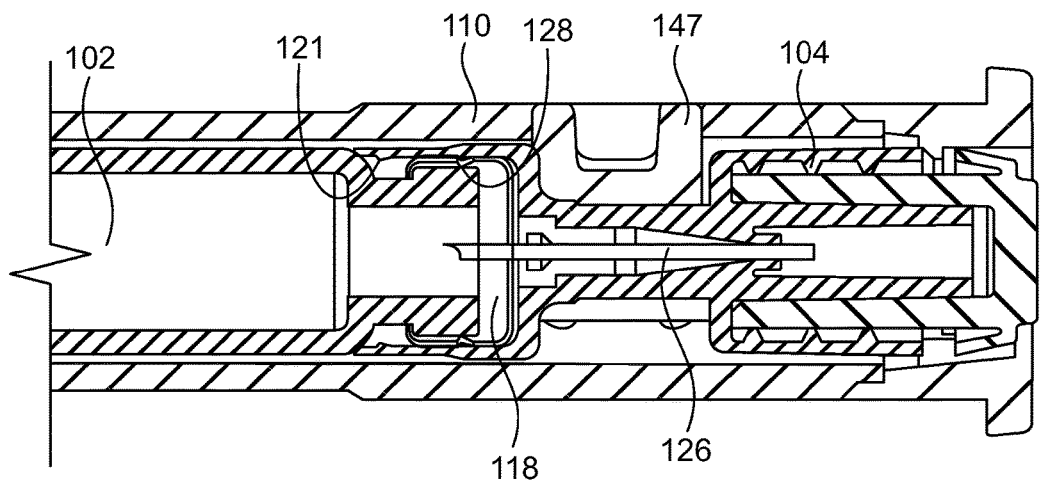
FIG. 10C is a cross section view of an example hub in an activated position.

The injection system 100 has an inactivated position (as shown in FIG. 10A) and a second, activated position (as shown in FIG. 10C). In the inactivated position, the piercing member 126 is positioned external to the fluid container 102, i.e., the piercing member 126 does not penetrate through the fluid seal 118. In the activated position, the piercing member 126 is positioned through the fluid seal 118 such that the interior 101 of the fluid container 102 is in fluid communication with an external environment of the fluid container 102 through the piercing member 126. Thus, when the injection system 100 is in the activated position, the pharmaceutical product contained in the fluid container 102 can be delivered to a patient (or transferred to another medical device) by the application of a distally-directed force to the plunger rod 108 in order to move the plunger 106 in the distal direction within the container 102 and force the liquid contained in the container 102 through the lumen of the piercing member 126.

Also in the activated position, fluids external to the container 102 can be aspirated into the fluid container 102 by the application of a proximally directed force to the plunger rod 108. Examples of fluids that can be aspirated include (i) additional pharmaceutical products or diluents for delivery to a patient, e.g., pharmaceutical products and/or diluents that are not otherwise compatible for long-term storage with the pharmaceutical product contained in the fluid container 102, or (ii) blood where the hub 104 has a hypodermic needle affixed thereto and where the hypodermic needle has been inserted into a patient's vascular system so as to allow the aspiration of blood into the fluid container 102, thereby providing a visual indication that the hypodermic needle is properly positioned within the patient's vasculature.

The injection system 100 may also include a housing 110 that substantially encompasses the fluid container 102 and the hub 104 while simultaneously allowing for relative coaxially movement between the fluid container 102 and the hub 104. The housing 110 at least partially surrounds the container 102 and protects the container 102 during shipment and handling. The housing 110 includes components for activation of the injection system 100 by creating axial movement of the fluid container 102 relative to the hub 104, as discussed in more detail below. Although the disclosure is described herein principally in connection with the embodiments in which the housing 110 and the fluid container 102 are physically separate components, it is to be appreciated that the housing 110 and the fluid container 102 can be physically separate components that are attached and/or be the same physical structure. By way of example, the housing 110 and the fluid container 102 can be the barrel of a standard syringe.

Figure 4:
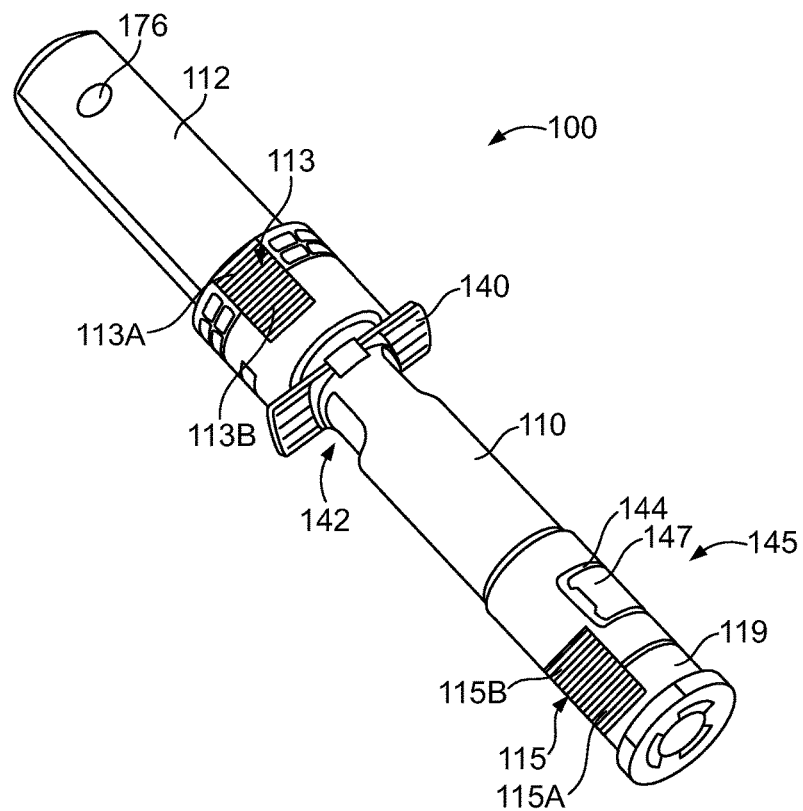
FIG. 4 is perspective view of the example injection system of FIG. 1.

As depicted in FIG. 4, a removable plunger rod cover 112 is releasably coupled to the housing 110. The plunger rod cover 112 defines an interior space that can be positioned over the plunger rod 108 to provide both protection from inadvertent, premature movement of the plunger rod 108 and protection from tampering or diversion of the pharmaceutical product contained in fluid container 102. In the absence of plunger rod cover 112, the contents of fluid container 102 could be accessed by inserting a needle or similar device through or around plunger 106, whereupon the contents of fluid container 102 could be withdrawn and/or added to using a needle or similar device. Plunger rod cover 112 and housing 110 are configured to be secured to one another by any number of configurations including, for example, complementary threads or a similar engagement that requires rotation of plunger rod cover 112 relative to housing 110 in order to remove plunger rod cover 112 from housing 110, thereby exposing the plunger rod 108.

In one embodiment, the injection system 100 includes a driver 114 mounted to the proximal portion 111 of the housing 110. The driver 114 is constructed to engage the fluid container 102 in order to impart a distally-directed axial force on the fluid container 102. The driver 114 is also constructed to engage a plunger rod cover 112. In one embodiment, the driver 114 and the plunger rod cover 112 are configured such that removal of the plunger rod cover 112 from the housing 110 causes the driver 114 to impart a distally-directed force on the fluid container 102 that results in distal, axial movement of the fluid container 102 relative to the housing 110. Because the housing 110 is configured to retain the hub 104 in order to prevent relative movement between the housing 110 and the hub 104, the distal axial movement of the fluid container 102 causes the system 100 to move from its inactivated position to its activated position, e.g., the fluid container 102 moves so as to cause the piercing member 126 to pass through the fluid seal 118 so as to allow for fluid flow into and/or out of the fluid container 102 through the piercing member 126. FIGS. 4 and 10A-10B show examples of an injection system 100 in the inactivated position. A removable hub cap 116 is positioned on a distal end of the housing 110. Hub cap 116 protects the dispensing end of hub 104 during storage and transportation of injection system 100. In some embodiments, the hub cab 116 includes a separate hub cap housing 119 that facilitates removal of the hub cap 116.

The plunger rod cover 112 may also include a surface on which at least a portion of a first tamper-evident band 113 can be mounted. A first portion 113A of the first tamper-evident band 113 may be mounted on plunger rod cover 112, and a second portion 113B of first tamper-evident band 113 may be mounted to the housing 110. First tamper-evident band 113 can be mounted through the use of a number of known techniques, including the use of adhesives and/or the use of a shrink-wrap material in construction of the first tamper-evident band 113. First tamper-evident band 113 is preferably scored, weakened, or perforated at a position between the first and second portions 113A, 113B to facilitate breaking thereof when a medical professional removes the plunger rod cover 112 from the housing 110 prior to use.

Figure 4A:
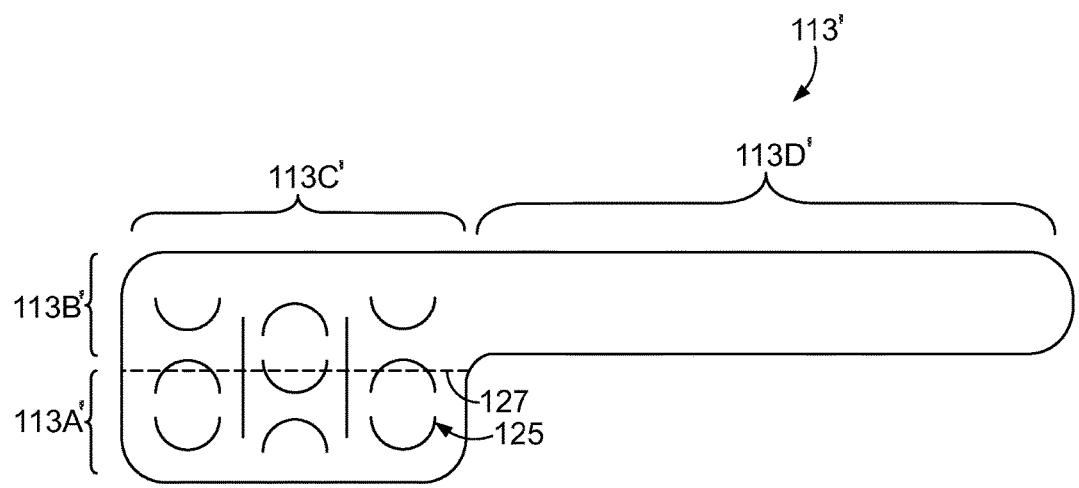
FIG. 4A is a side view of an example tamper-evident band.

FIG. 4A illustrates another example tamper-evident band 113'. Like the tamper-evident band 113 illustrated in FIG. 4, the tamper-evident band 113' includes a first portion 113A' configured to be coupled to the plunger rod cover 112 and a second portion 113B' configured to be coupled to the housing 110. The first portion 113A' and the second portion 113B' define an evidence portion 113C' of the tamper-evident band 113'. The tamper-evident band 113' further includes a band portion 113D' extending from the evidence portion 113C'. It may be desirable to construct the evidence portion 113C' to have a sufficient size to provide a force inhibiting inadvertent rotation of the plunger rod cover 112 relative to the housing 110 and, thus, inadvertent activation of the injection system 100. However, constructing the evidence portion 113C' to be too large can make the injection system 100 more difficult to activate because the larger the evidence portion 113C', the greater the amount of torque a user needs to apply to the plunger rod cover 112 to break the tamper-evident band 113' (i.e., the "torque threshold") and activate the injection system 100.

One way to control the amount of torque required to activate the injection system 100 is to limit the extent to which band 113, 113' extends around the injection system 100. It will be appreciated that the longer band 113, 113' is the greater the torque required to activate injection system 100. In one embodiment of the present invention band 113, 113' extends approximately two-third of the way around the circumference of injection system 100.

Also, as shown in FIG. 4A, the tamper-evident band 113, 113' can include multiple perforations 125 that facilitate breaking of the tamper-evident band 113, 113' in response to a threshold torque applied between the plunger rod cover 112 and the housing 110. The perforations 125 include multiple line-shaped perforations positioned between multiple semi-circle-shaped perforations. The line shaped perforations can be arranged perpendicularly to an axis 127 along which the tamper-evident band 113' is intended to break. By arranging the line-shaped perforations perpendicularly to the axis 127, the tamper-evident band 113, 113' is less likely to inadvertently break due to bending of the injection system 100. The perforation lines can also be arranged parallel to the axis 127.

The semi-circle-shaped perforations tend to reduce the occurrence of sharp corners which can create undesirable lifting of edges due to minimal adhesive at the apexes of the sharp corners. Such sharp corners are formed, for example, at the center of "X" shaped perforation patterns.

Second tamper-evident band 115 may be provided such that a first portion 115A of second tamper-evident band 115 may be mounted to hub cap housing 119 and a second portion 115B of second tamper-evident band 115 may be mounted to housing 110. Hub cap housing 119 is constructed to be removably attached to housing 110. For example, hub cap housing 119 and housing 110 can be provided with complementary screw threads that allow hub cap housing 119 and housing 110 to be threadably connected and disconnected from one another. In an alternative embodiment, hub cap housing 119 is configured to frictionally attach to housing 110 such that hub cap housing 119 can be removed therefrom. Hub cap housing 119 and hub cap 116 are preferably configured such that they are attached when hub cap housing 119 is moved into close proximity with hub cap 116. This attachment can be a frictional attachment, a threaded attachment, a latching attachment, or a variety of other known means for providing a mechanical attachment. Second tamper-evident band 115 can be scored, weakened, or perforated in order to facilitate removal of hub cap housing 119 (per the discussion of the first tamper-evident band 113). Accordingly, the second tamper-evident band 115 is broken when a medical professional removes the hub cap housing 119 from the housing 110. Also, because of the attachment of the hub cap housing 119 to the hub cap 116, removal of the hub cap housing 119 from the housing 110 simultaneously results in removal of the hub cap 116 from the hub 104.

The first and second tamper evident bands 113, 115 may be in the form of a strip, tape, or shrink tape as readily understood by those of skill in the art. Either or both of the first and second tamper-evident bands 113, 115 may contain labeling or other printed design or information thereon. The information may include, by way of example, information regarding the pharmaceutical product contained in the fluid container 102 and/or directions for operation and use of the injection system 100.

The distal end of housing 110 may include an opening 144 and a locking mechanism 145 that facilitate insertion and axial securement of the fluid container 102 within the housing 110. The locking mechanism 145 can have a variety of forms but in the depicted embodiment includes a clip 147 configured for insertion through the opening 144 after the fluid container 102 is positioned within the housing 110. With the fluid container 102 positioned within the housing 110, the hub 104 is positioned adjacent to the opening 144. Inserting the clip 147 through opening 144 secures the clip 147 to the hub 104. Once the clip 147 is secured to the hub 104, relative axial movement between the hub 104 and the housing 110 is prevented by the clip 147 (which is either integrally formed with the housing 110 or is constructed to engage the periphery of the opening 144 in order to prevent relative axial movement between the hub 104 and the housing 110). In one embodiment, the removal of the plunger rod cover 112 from the housing 110 causes the injection system 100 to be moved from a first, inactivated, position to a second, activated, position as a result of axial movement of the fluid container 102 relative to the housing 110 and the hub 104 which is fixed in the housing 110 as above-discussed. In this embodiment, removal of the plunger rod cover 112 forces the driver 114 to move axially in a distal direction relative to the housing 110. In turn, the driver 114 urges the fluid container 102 in the distal direction within the housing 110 such that the piercing member 126 is pushed through the fluid seal 118, thereby moving injection system 100 from the inactivated position to the activated position.

Figure 5:
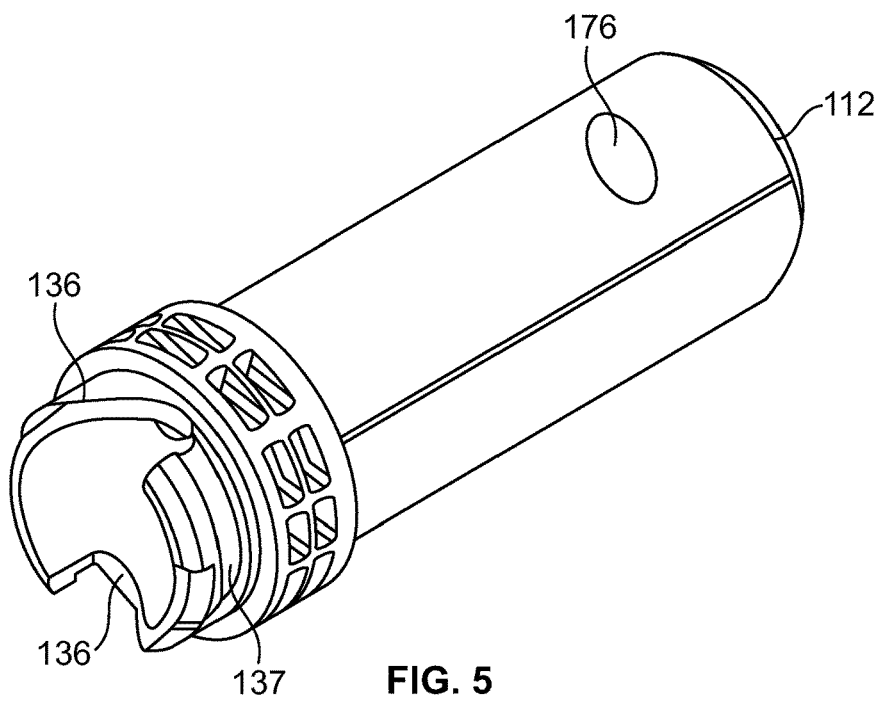
FIG. 5 is a perspective view of an example plunger rod cover.
Figure 6:
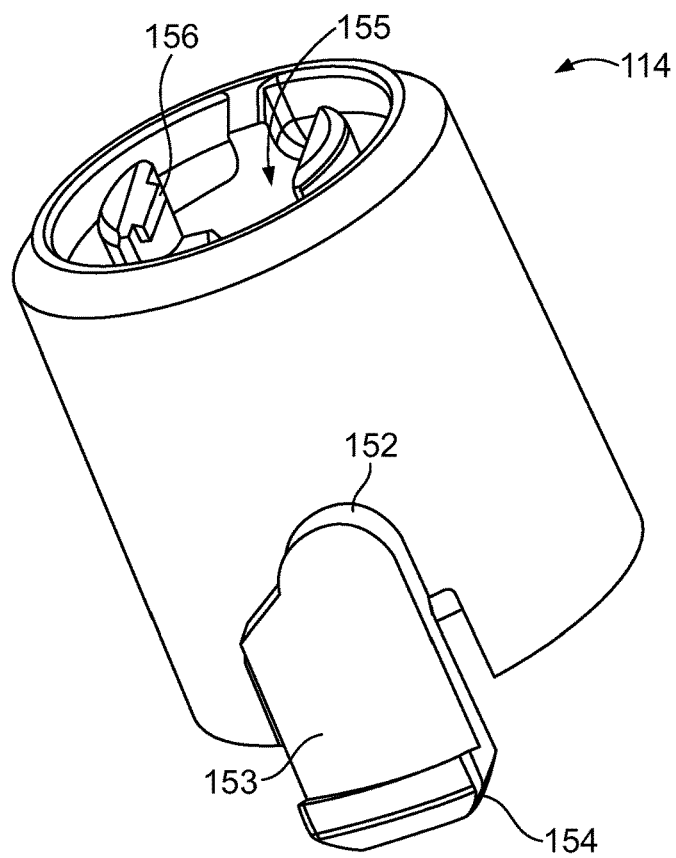
FIG. 6 is a perspective view of an example driver.

In the embodiment depicted in FIGS. 5 and 6, the plunger rod cover 112 and the driver 114 include complementary cam surfaces 136 and 152. The cam surfaces 136 and 152 are configured to move the driver 114 in a distal direction upon rotation of the plunger rod cover 112 relative to the housing 110 when the cover 112 is removed from the housing 110 by rotation. Movement of the driver 114 in the distal direction moves the container 102 in the distal direction within the housing 110.

The cam surfaces 136, 152 can be constructed from materials that provide a sufficient coefficient of friction and are capable of withstanding the torques applied by the user during activation. In some examples, the driver 114 can be constructed from a variety of materials including polyoxymethylene, an acetal homopolymer resin (e.g., DELRIN provided by DUPONT), and/or polypropylene with a silicone lubricant additive. Additionally, in some examples, the plunger rod cover 112 can be constructed from a styrene acrylic and/or polycarbonate material. Depending on the materials used for the driver 114 and the plunger rod cover 112, one or both of the cam surfaces 136, 152 can be roughened to improve the coefficient of friction between the cam surfaces 136, 152. For example, the coefficient of friction for the engagement of the cam surfaces 136, 152 can be approximately 0.0 to approximately 0.20.

Figure 7:
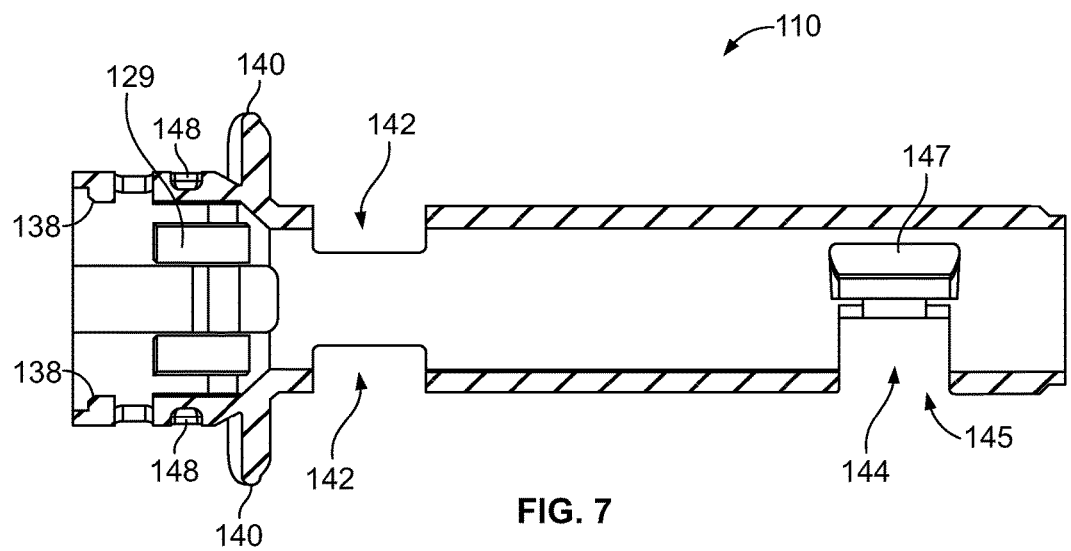
FIG. 7 is a cross section view of an example housing.

The housing 110 can include one or more slots 129 as shown in FIGS. 1 and 7. In the illustrated example, the slots 129 are oriented generally in a direction from the proximal end to the distal end and arranged around the periphery of the housing 110; however, it should be understood that the slots 129 can be oriented and arranged differently according to other examples.

Figure 8:
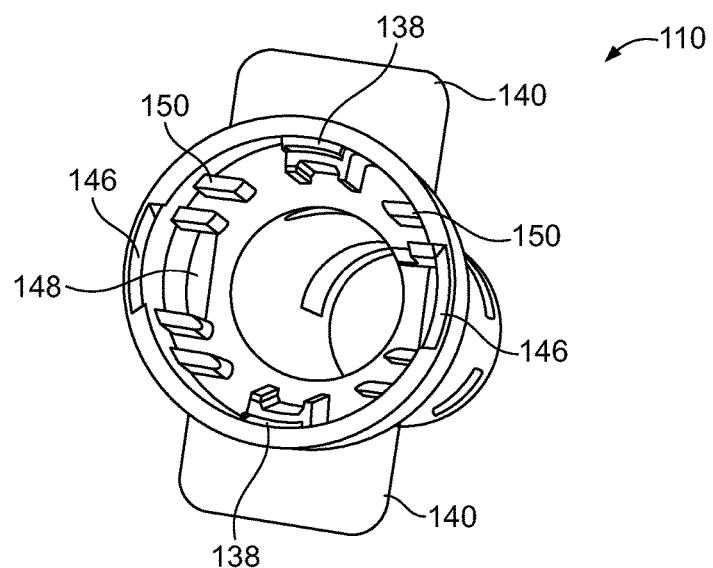
FIG. 8 is a perspective view of a proximal end of the example housing of FIG. 7.

As shown in FIGS. 7 and 8, the proximal portion 111 of the housing 110 may include one or more pawls 138 formed on an interior of the housing 110. The pawls 138 are configured to ride in tracks 137 of the plunger rod cover 112 (see FIG. 5) to provide a thread-like engagement between the housing 110 and the plunger rod cover 112. The cam surfaces 136 of the plunger rod cover 112 may also interact with the pawls 138 formed on the housing 110 to effectively push the plunger rod cover 112 away from the housing 110 when the plunger rod cover 112 is rotated beyond a point at which the pawls 138 leave the tracks 137 formed on the interior surface of the plunger rod cover 112. In other words, the pawls 138 contact the cam surfaces 136 such that, upon rotation of the plunger rod cover 112, the plunger rod cover 112 is pushed away from the proximal portion 111 of the housing 110 due to interaction between the pawls 138 and the ramped cam surfaces 136.

As described above, the driver 114 is axially movable relative to the housing 110. To facilitate such movement, the housing 110 can include channels 146 formed on the interior wall at the proximal portion 111 of the housing 110, as shown in FIG. 8. The channels 146 are configured to receive corresponding arms 153 of the driver 114 (see FIG. 6) and allow for linear, axial movement of the driver 114 relative to the housing 110. The channels 146 and the arms 153 are further configured to prevent rotation of the driver 114 relative to the housing 110. The distal ends of the channels 146 terminate at apertures 148 that are constructed to receive tabs 154 extending from the distal end of the arms 153 in order to retain the driver 114 relative to the housing 110 when the tabs 154 are locked within the apertures 148. The arms 153 are resilient such that the tabs 154 extend in a distal direction beyond the distal end of the driver 114, thereby providing a flexible, cantilevered configuration used to enable the driver 114 to be locked to the housing 110 upon activation. The tabs 154 move radially outwardly through the channels 146 of the housing 110 upon activation of the injection system 100, which axially and rotationally locks the driver 114 and the housing 110. While the cam surface 152 is shown as being associated with the arm 153 of the driver 114 in FIG. 6, one of skill in the art will understand that these features may be readily configured as separate components on the driver 114.

Housing 110 may additionally include one or more centering ribs 150 formed on the interior surface of the housing 110 to assist in aligning the arms 153 of the driver 114 with the channels 146 of the housing 110. The housing 110 can include other features. In the embodiment depicted in FIG. 4, the housing 110 includes finger grips 140 positioned proximal to the point at which the housing 110 and the plunger rod cover 112 are connected. Apertures 142 are defined in the housing distally of the finger grips 140 as depicted in FIG. 4.

Figure 9:
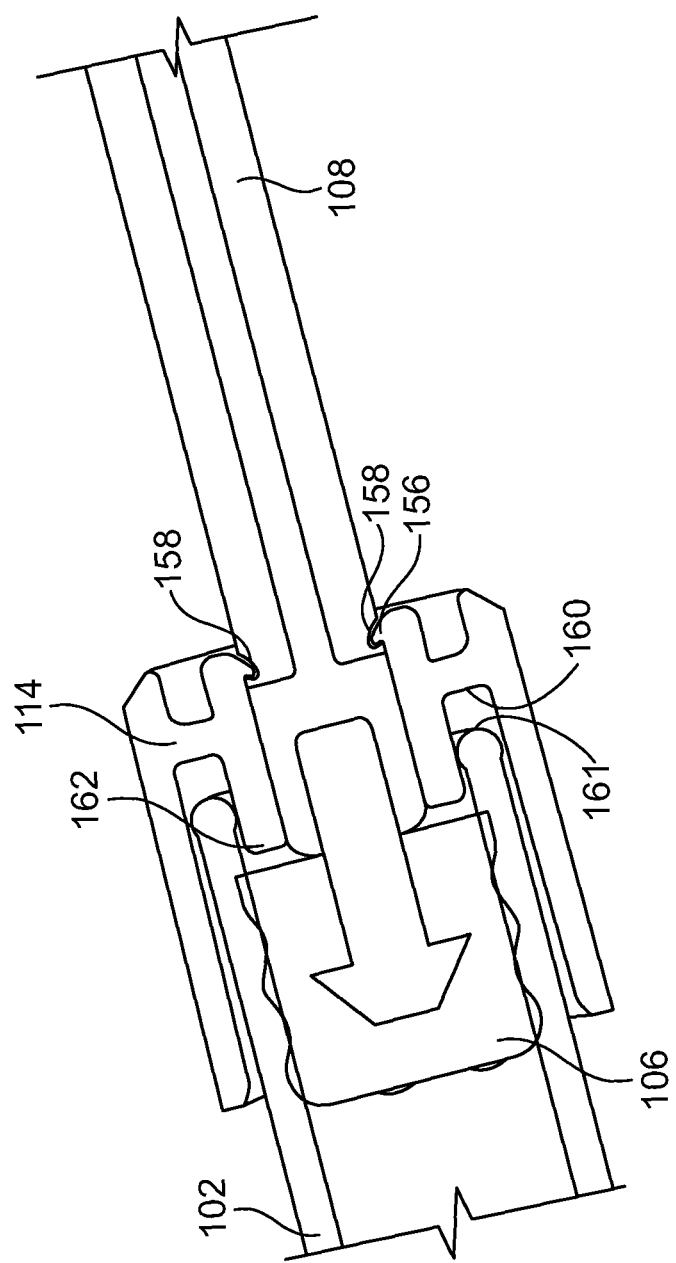
FIG. 9 is a cross section view of aspects of the system shown in FIG. 1.

As shown in FIG. 9, the driver 114 may include detents 156 located on the proximal end of the driver 114. The detents 156 may be configured to releasably engage a complementary recess 158 on the plunger rod 108 in order to releasably secure the plunger rod 108 and the driver 114. Detent retention may be overcome by pushing the plunger rod 108 with sufficient force to advance the detent 156 out of the recess 158.

The plunger rod 108 and the plunger 106 may be connected by any known means, including the use of threads 134 on the plunger rod 108 whereby the plunger rod 108 can be threadably secured to plunger 106 during assembly of injection system 100. Alternatively, connection of plunger rod 108 to plunger 106 can utilize a snap fit or other frictional connection known to those of ordinary skill in the art. Those skilled in the art will appreciate that the connecting member can have other configurations providing locking or frictional connections between plunger 106 and plunger rod 108.

Driver 114 may also include an annular surface 160 near the proximal end of driver 114. The annual surface 160 may be configured to engage the annular proximal end surface of the fluid container 102 in order to move the fluid container 102 axially in a distal direction to the activated position upon rotation of the plunger rod cover 112 relative to the housing 110. The driver 114 may further include an additional stop surface 162 that projects radially inwardly from the annular surface 160. The stop surface 162 is configured to engage the plunger 106 to prevent the plunger 106, and the plunger rod 108 attached thereto, from being backed out of the fluid container 102. This prevents removal of the plunger 106 from the fluid container 102 and reduces the possibility of inadvertent or purposeful removal of the pharmaceutical product from the fluid container 102 through the proximal end 109. In combination, plunger rod 108 and the driver 114 also help to prevent unauthorized access to the pharmaceutical product within the fluid container 102 by preventing a hypodermic needle (or similar device) from being inserted through or around the plunger 106 in order to tamper with and/or divert the pharmaceutical contents of the fluid container 102.

Apertures 142 formed distally from finger grips 140 permit the user to rotate fluid container 102 inside of housing 110, which allows for easy viewing of a label or other marking on fluid container 102 that is positioned to be read through apertures 142.

FIGS. 10A and 10B illustrate the injection system 100 in an inactivated state. When the injection system 100 is in the inactivated state, the piercing member 126 does not pierce the fluid seal 118, the plunger rod cover 112 is secured to the housing 110, and the driver 114 is position at the proximal end of housing 110.

Figure 10D:
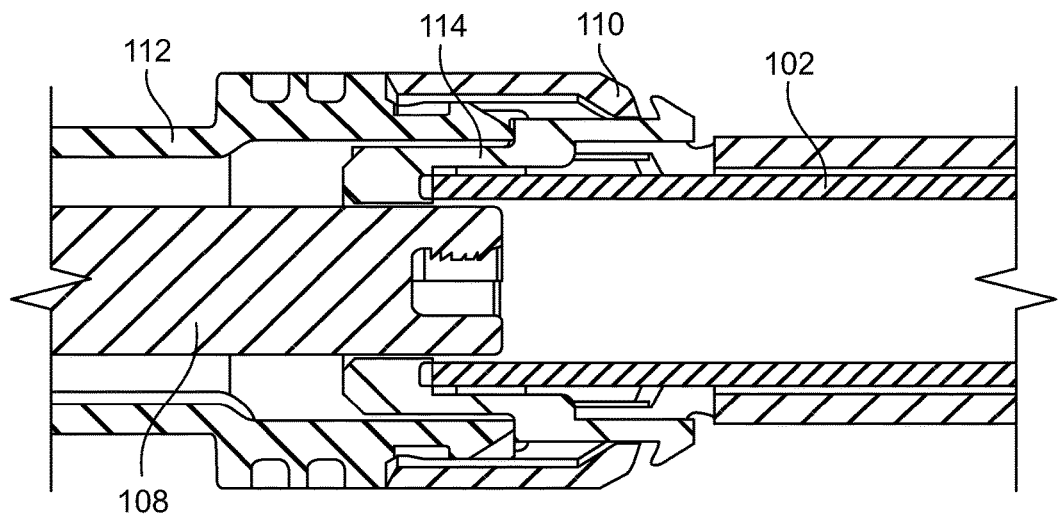
FIG. 10D is a cross section view of an example driver in an activated position.

FIGS. 10C-10D illustrate the injection system 100 in an activated state. After activation, detents 154 of the driver 114 snap into the apertures 148 of the housing 110 to prevent pull-out of the plunger 106, the plunger rod 108, and the driver 114 as shown in FIG. 10D.

In operation, a medical professional can activate the injection system 100 by rotating the plunger rod cover 112 relative to the housing 110, thereby moving the driver 114 axially in the distal direction and in turn causing the fluid container 102 to advance axially in the distal. Because the hub 104 is secured in the housing 110 and precluded from moving distally, the application of a distally-directed force on the fluid container 102 causes the fluid container 102 to slide axially within the housing 110 such that the piercing member 126 passes through the fluid seal 118, thereby transitioning the injection system 100 from its inactivated state to its activated state. As discussed above, the action of the rotating plunger rod cover 112 relative to the housing 110 breaks the first tamper-evident seal 113 and the plunger rod cover 112 from the housing 110, thereby exposing the plunger rod 108.

The distal portion of the hub 104 includes a connecting portion 124 that is configured to deliver the pharmaceutical product contained in the container 102 directly to a patient or to another medical delivery device. It will be appreciated that connecting portion 124 can have a variety of configurations, including, for example, (i) a standard medical luer connector; (ii) a threaded luer connector; (iii) a hypodermic needle for delivery of pharmaceutical products directly to a patient or for indirect delivery through a pierceable septum (e.g., a pierceable septum associated with an add port of a tube set or an add port of a flexible pharmaceutical container), (iv) a blunt needle for delivery of pharmaceutical products to another medical device having the capability of receiving a pharmaceutical product from a blunt needle (e.g., a pre-slit elastomeric seal on a tube set or a flexible pharmaceutical container), and/or (v) fitting that allows for another device, e.g., a hypodermic needle, to be attached to the connecting portion 124.

As depicted, the connecting portion 124 includes a collar 117 having radially inwardly facing threads 122 and a centrally located male luer 123. As such, the connecting portion 124 is designed as a male locking luer configured to mate with a complementary female luer fitment of a delivery device.

Figure 11:
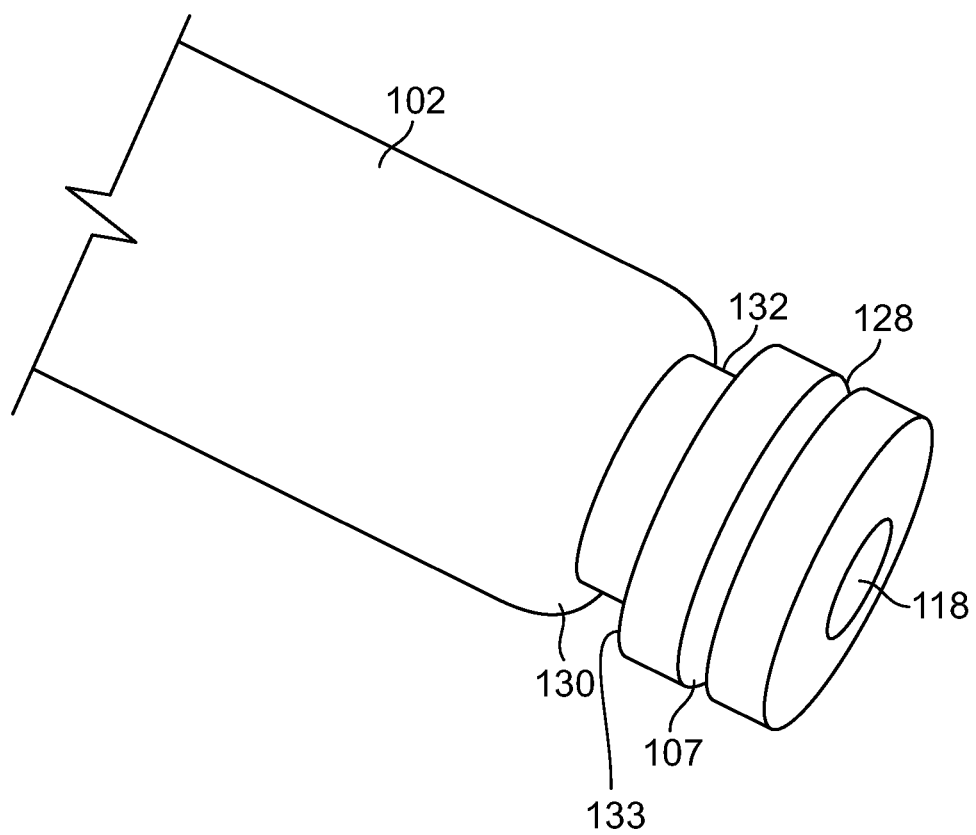
FIG. 11 is a plan view of a distal end of an example container.

In one embodiment, the cavity 120 of the proximal portion 105 of the hub 104 has a radially inwardly facing annular bead 121. The bead 121 is configured to engage a complementary annular groove 128 on the distal end portion 107 of fluid container 102 (see FIG. 11). This snap-type engagement helps maintain sterility of the piercing member 126 by preventing access thereto, and helps minimize or eliminate premature activation of the injection system 100 by increasing the force required to impart relative movement between the hub 104 and the fluid container 102.

Once the injection system 100 is in the activated position, the annular bead 121 no longer engages the groove 128 on the distal portion of the container 102. Instead, the annular bead 121 moves proximally with respect to the distal portion of the container 102. Similarly, the annular groove 128 moves distally with respect to the proximal end 105 of the hub 104. The axial displacement of the bead and annular groove can vary. In one embodiment, after activation the bead abuts a first shoulder 130 at a necked-down portion 132 near the distal portion 107 of the container 102. Because the inner diameter of the bead 121 is less than an outer diameter of a second shoulder 133 between the neck-down portion 132 and the distal end 107, the hub 104 is prevented from moving back in the distal direction after activation. This helps to ensure that the injection system 100 remains in the activated state.

Figure 12:
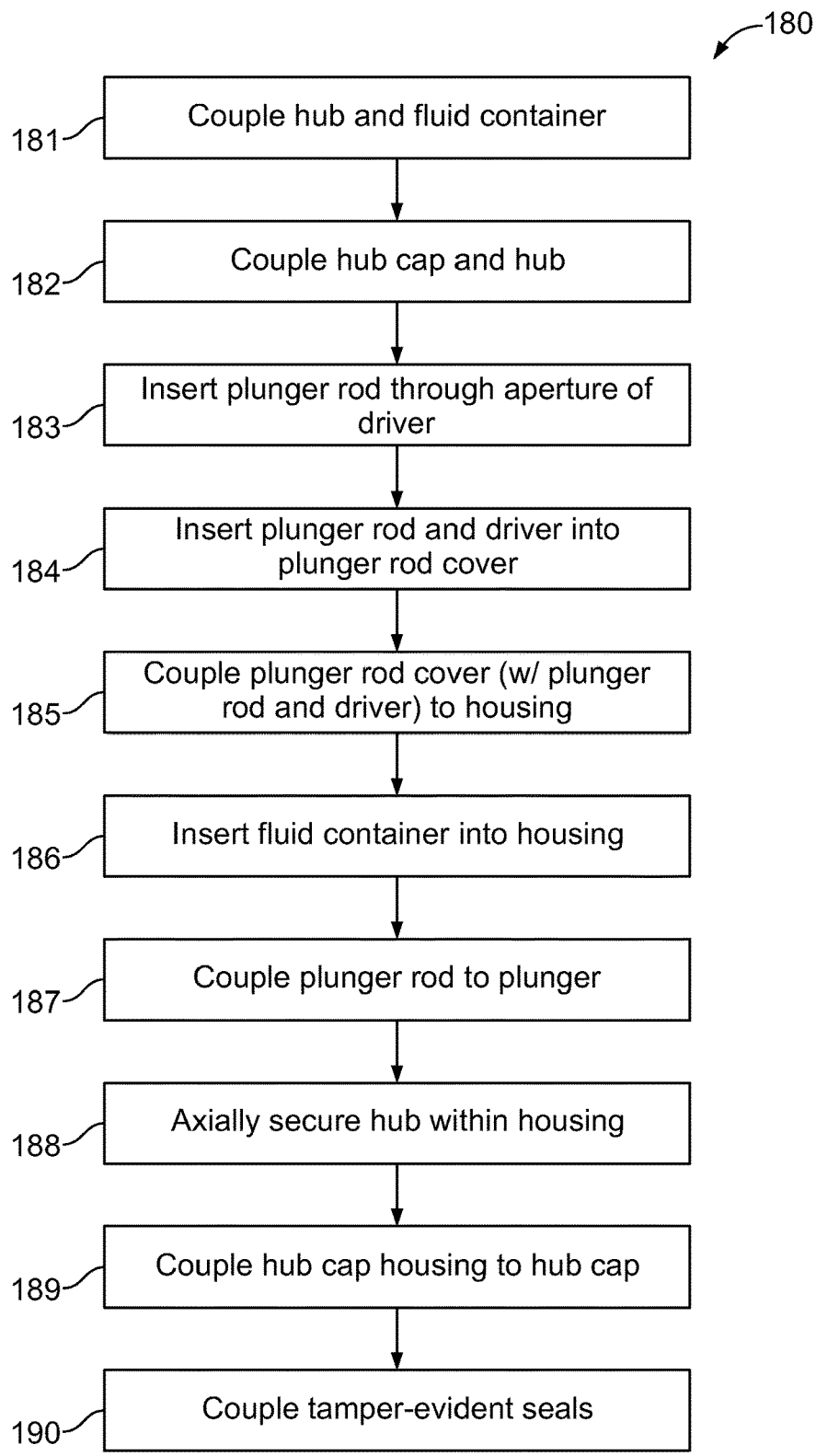
FIG. 12 is an example flowchart of a method of assembly of the injection system.

Referring now to FIG. 12, an example process 180 is illustrated for assembling the injection system 100 according to aspects of the disclosure. At block 181, the hub 104 is coupled to the fluid container 102 in the inactivated-hub position. For example, the distal end 107 of the container 102 can be inserted into the cavity 120 of the hub 104 until the bead 121 on the hub 104 engages the groove 128 on the distal end 107 of the container 102. At block 182, the hub cap 116 is coupled to the connecting portion 124 of the hub 104. This forms a first sub-assembly comprising the fluid container 102, the hub 104, and the hub cap 116.

At block 183, the plunger rod 108 is inserted through the aperture 155 of the driver 114. Next, the plunger rod 108 and the driver 114 are inserted into the plunger rod cover 108 at block 184. At block 185, with the plunger rod 108 and driver 114 received in the plunger rod cover 112, the plunger rod cover 112 is coupled to the proximal portion 111 of the housing 110. To do so, the arms 153 on the driver 114 may be aligned with the channels 146 on the housing 110. As a result of block 185, the housing 110, the plunger rod cover 112, the driver 114, and the plunger rod 108 form a second sub-assembly.

The first and second sub-assemblies may then be assembled to form the injection system 100. At block 186, the proximal end 109 of the fluid container 102 is inserted into the housing 110. As a result of block 186, the proximal side 106B of the plunger 106 engages the plunger rod 108. At block 187, the plunger 106 is coupled to the plunger rod 108. For example, at block 187, the fluid container 102 can be rotated to cause the plunger rod 108 to threadably couple to the plunger 106. As a result, at least a portion of the plunger rod 108 is positioned externally to the fluid container 102 and enclosed by the plunger rod cover 112. At block 188, the clip 147 is closed to secure the hub 104 within the housing 110. At block 189, the hub cap housing 119 is coupled to the hub cap 116, for example, by a snap-fit engagement. At block 190, the first tamper-evident band 113 is coupled to the housing 110 and the plunger rod cover 112, and the second tamper-evident band 115 is coupled to the hub cap housing 119 and the housing 110.

Figure 13:
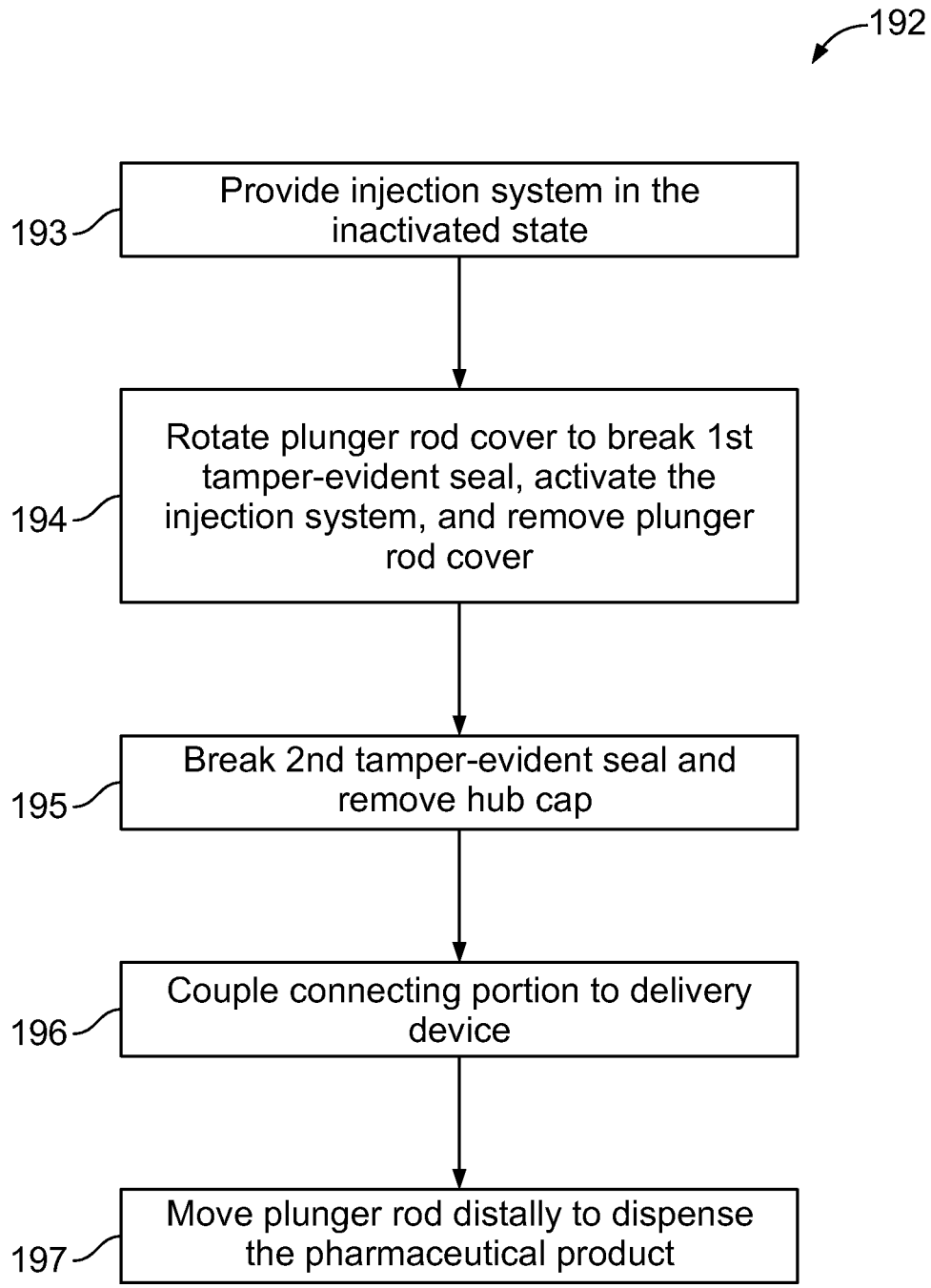
FIG. 13 is an example flowchart of a method of delivering a pharmaceutical product using the injection system.

Referring now to FIG. 13, an example process 192 is illustrated for delivering a pharmaceutical product to a patient according to aspects of the disclosure. At block 193, the injection system 100 is provided in the inactivated state. At block 194, the injection system 100 is activated by rotating the plunger rod cover 112 relative to the housing 110. The driver transduces the rotation of the plunger rod cover 112 to cause the fluid container 102 to advance axially in the distal direction. Because the hub 104 is secured in the housing 110 and inhibited from moving distally, the fluid container 102 moves axially relative to the hub 104 to transition the hub 104 from the inactivated-hub position to the activated-hub position. As a result, the piercing member 126 passes through the fluid seal 118, thereby transitioning the injection system 100 from the inactivated state to the activated state. As described above, rotating the plunger rod cover 112 relative to the housing 110 also breaks the first tamper-evident seal 113 and removes the plunger rod cover 112 from the housing 110, thereby exposing the plunger rod 108. Accordingly, rotating the plunger rod cover 112 at block 184 breaks the tamper-evident seal 113, activates the system 100, and exposes the plunger rod 108 for use.

At block 195, the user removes the hub cap 116 to expose the connecting portion 124. Removal of the hub cap 116 results in the breaking of the second tamper-evident seal 115. For example, the user may break the second tamper-evident seal 115 by rotating the hub cap housing 119 relative to the housing 110. The connecting portion 124 may then be coupled to a delivery device (e.g., a needle, a luer connector, etc.) or otherwise prepared for delivery of the pharmaceutical product at block 196. Then, at block 197, the plunger rod 108 is moved toward the distal end 107 to dispense the pharmaceutical product from the fluid container 102 at the distal end 107.

It should be understood that, according to alternative aspects of the disclosure, the processes 180, 192 of FIGS. 12-13 can omit steps, include additional steps, and/or modify the order of steps. Additionally, it is contemplated that one or more of the steps can be performed simultaneously.

Various examples of an injection system in accordance with the disclosure have been described above. Those skilled in the art will understand, however, that changes and modifications may be made to those examples without departing from the scope of the appended claims.

We claim:

1. An injection system, comprising:
    a container configured to contain a pharmaceutical product, the container having a proximal end, a distal end, and an inner surface extending between the proximal end and the distal end;
    a plunger positioned within the container and having a surface that slidably engages the inner surface of the container;
    a plunger rod connected to the plunger, the plunger rod extending from the plunger such that at least a portion of the plunger rod is positioned externally to the proximal end of the container;
    a housing at least partially surrounding the container;
    a plunger rod cover removably coupled to the housing and enclosing the portion of the plunger rod positioned externally to the container, the plunger rod cover being configured to be removed from the housing to allow access to the plunger rod, wherein removal of the plunger rod cover moves the container from an inactivated position to an activated position; and
    a driver positioned at the proximal end of the container and configured to transduce rotation of the plunger rod cover relative to the housing into linear movement of the container relative to the housing.

2. The injection system of claim 1, wherein the container further comprises a fluid seal fluidly sealing the distal end of the container and a hub movably mounted on the distal end of the container, the hub including a piercing member constructed to pass through the seal, the hub being movable relative to the container between a first position in which the piercing member is positioned externally to the container and a second position in which the piercing member is disposed through the seal such that the piercing member is in fluid communication with an interior of the container, wherein the hub is in the first position when the container is in the inactivated position and wherein the hub is in the second position when the container is in the activated position.

3. The injection system of claim 1, wherein the driver and the plunger rod cover include complementary cam surfaces constructed to linearly move the driver in response to rotation of the plunger rod cover relative to the housing.

4. The injection system of claim 3, wherein one of the cam surfaces comprises a roughened surface.

5. The injection system of claim 1, wherein the driver includes a stop surface configured to engage the plunger so as to inhibit the plunger from being removed from the container.

6. The injection system of claim 1, further comprising a tamper-evident band coupled to the plunger rod cover and the housing whereby relative movement between the plunger rod cover and the housing is configured to break the tamper-evident band.

7. The injection system of claim 6, further comprising: a hub cap positioned on a distal end of the hub; and a second tamper-evident band coupled to the hub cap and the housing, whereby relative movement between the hub cap and the housing is configured to break the second tamper-evident band.

8. An injection system, comprising:
a container configured to contain a pharmaceutical product, the container having a proximal end, a distal end, and an inner surface extending between the proximal end and the distal end; a plunger positioned within the container and having a surface that slidably engages the inner surface of the container;
a plunger rod connected to the plunger, the plunger rod extending from the plunger such that at least a portion of the plunger rod is positioned externally to the proximal end of the container;
a housing at least partially surrounding the container; and
a plunger rod cover removably coupled to the housing and enclosing the portion of the plunger rod positioned externally to the container, the plunger rod cover being configured to be removed from the housing to allow access to the plunger rod, wherein removal of the plunger rod cover moves the container from an inactivated position to an activated position;
wherein the housing includes a pawl that is configured to engage a cam surface on the plunger rod cover such that rotation of the plunger rod cover relative to the housing causes the plunger rod cover to be moved away from the housing.

9. An injection system comprising:
a container having a proximal end, a distal end, and an interior surface, the interior surface defining a cavity for containing a pharmaceutical product;
a plunger disposed in the cavity defined by the container, the plunger having a surface constructed to sealingly engage the interior surface of the container whereby a seal is maintained between the plunger and the interior surface of the container as the plunger is moved within the cavity;
a plunger rod attached to the plunger, the plunger rod extending proximally from the plunger such that a portion of the plunger rod is disposed externally to the container;
a housing at least partially surrounding the container;
a plunger rod cover defining an interior space, the plunger rod cover being removably attached to the housing; and a driver mounted on the housing, the driver being configured to engage the plunger rod cover when the injection system is in a first, inactivated state, the driver further being configured to move the injection system from the first, inactivated state to a second, activated state upon removal of the plunger rod cover from the housing;
wherein the plunger rod cover is constructed to be removed by rotating the plunger rod cover relative to the injection system.

10. The injection system in accordance with claim 9, wherein the container has a pierceable fluid seal fluidly sealing the distal end thereof, the container further comprising a hub movably mounted to the distal end of the container, the hub having a piercing member constructed to pierce the pierceable fluid seal, the hub having a first position in which the piercing member is disposed externally to the cavity defined by the container and a second position in which the piercing member is disposed through the pierceable fluid seal whereby the interior of the cavity is in fluid communication with an external environment through the piercing member.

11. The injection system of claim 9, wherein the driver includes a stop surface configured to engage the plunger so as to inhibit the plunger from being removed from the container.

12. The injection system of claim 9, further comprising a tamper evident seal associated with the plunger rod cover, wherein removal of the plunger rod cover breaks the seal.

13. A method for delivering a pharmaceutical product comprising: providing an injection system comprising:
a container containing the pharmaceutical product, the container having a proximal end, a distal end, and an inner surface extending between the proximal end and the distal end, the inner surface of the container defining an interior volume for containing the pharmaceutical product;
a plunger positioned within the container and having a surface that slidably engages the inner surface of the container;
a plunger rod connected to the plunger, the plunger rod extending from the plunger such that at least a portion of the plunger rod is positioned externally to the proximal end of the container;
a plunger rod cover removably coupled to a housing at least partially surrounding the container, the plunger rod cover enclosing the portion of the plunger rod positioned externally to the container, the plunger rod cover being configured to be removed from the housing to allow access to the plunger rod; and
a driver constructed to transduce rotation of the plunger rod cover to transition the injection system from an inactivated state in which the pharmaceutical product in the container cannot be delivered therefrom to an activated state in which the pharmaceutical product in the container can be delivered from the container;
rotating the plunger rod cover and removing the plunger rod cover from the housing, thereby transitioning the injection system from the inactivated state to the activated state; and
applying a distally directed force to the plunger rod in order to deliver the pharmaceutical product from the container.

* * * * *

UNITED STATES PATENT AND TRADEMARK OFFICE
CERTIFICATE OF CORRECTION

PATENT NO. : 10,039,887 B2
APPLICATION NO. : 14/815669
DATED : August 7, 2018
INVENTOR(S) : John Sundquist et al.

It is certified that error appears in the above-identified patent and that said Letters Patent is hereby corrected as shown below:

On the Title Page

Item [72], after "John Coleman Horton" insert --IV--

Signed and Sealed this
Thirtieth Day of October, 2018

Andrei Iancu
*Director of the United States Patent and Trademark Office*